United States Patent [19]

Ghanta et al.

[11] Patent Number: 5,814,332
[45] Date of Patent: Sep. 29, 1998

[54] PROCEDURE FOR ENCAPSULATING IBUPROFEN

[75] Inventors: Sambasiva Rao Ghanta, Centerville; Robert Edmon Guisinger, Dayton, both of Ohio

[73] Assignee: Eurand America, Inc., Vandalia, Ohio

[21] Appl. No.: 804,091

[22] Filed: Feb. 20, 1997

Related U.S. Application Data

[62] Division of Ser. No. 483,909, Jun. 7, 1995, Pat. No. 5,653,993, which is a continuation of Ser. No. 106,024, Aug. 13, 1993.

[51] Int. Cl.⁶ ..................................................... A61K 9/68
[52] U.S. Cl. ........................ 424/440; 424/456; 424/492; 424/478
[58] Field of Search ................................... 424/440, 489, 424/456, 494

[56] References Cited

U.S. PATENT DOCUMENTS

| | | | |
|---|---|---|---|
| 4,460,563 | 7/1984 | Calanchi | 424/35 |
| 4,462,982 | 7/1984 | Samejima et al. | 424/35 |
| 4,766,012 | 8/1988 | Valenti | 427/213.36 |
| 4,835,186 | 5/1989 | Reuter | 514/570 |
| 4,835,187 | 5/1989 | Reuter | 514/570 |
| 4,835,188 | 5/1989 | Ho | 514/570 |
| 4,937,254 | 6/1990 | Sheffield et al. | 424/497 |
| 4,952,402 | 8/1990 | Sparks et al. | 424/470 |
| 5,215,755 | 6/1993 | Roche et al. | 424/480 |

OTHER PUBLICATIONS

H.P. Merkle et al "Preparation and In Vito Evaluation of Cellulose Acetate Phthalate Coacervate Microcapsules", J. Pharm Science 62 pp. 1444–1448 (1973).

J.R. Nixon et al "The In Vitro Evaluation of Gelatin Coacerrate Microcapsules", J. Pharm Pharmac, 1971, 23 Suppl. 1475–1555.

*Primary Examiner*—Thurman K. Page
*Assistant Examiner*—William E. Benston, Jr.
*Attorney, Agent, or Firm*—John W. Routh

[57] ABSTRACT

This disclosure is directed to preparation of individual taste-masked, high bioavailability, high payload, microcapsules by microencapsulation of water-insoluble NSAID drug materials in the substantial absence of microcapsule agglomerates. These taste-masked microcapsules contain a high payload, e.g., about 83+ wt. % of said NSAID drug material having high bioavailability and can then be formulated into chewable tablets and liquid aqueous suspensions for medicinal use. Both cellulose acetate phthalate and gelatin are the microencapsulating polymer wall material.

Control of pH, controlled addition of a Hofmeister (lyotropic) salt, microencapsulation of the water-insoluble NSAID medicament with a liquid phase of both cellulose acetate phthalate and gelatin microencapsulating material and the subsequent insolubilization of said liquid encapsulating material after it is wrapped around the medicament core with dilute acid are important process parameters to achieving the proper individual microcapsules to obtain highly bioavailability taste-masked, water-insoluble NSAID drug materials, esp., naproxen and ibuprofen, by microencapsulation alone.

5 Claims, No Drawings

PROCEDURE FOR ENCAPSULATING IBUPROFEN

This application is a divisional application of application Ser. No. 483,909, filed June 7, 1995 now U.S. Pat. No. 5,653,993 which in turn was a continuation of Ser. No. 106,024, filed August 13, 1993.

BRIEF DESCRIPTION OF THE INVENTION

The present invention is directed to preparation of individual taste-masked, high bioavailability, high payload, microcapsules by simultaneous micro-encapsulation of water-soluble NSAID drug materials in the substantial absence of microcapsule agglomerates. These taste-masked microcapsules contain a high payload, e.g., about 83+ wt. % of said NSAID drug material having high bioavailability and can be formulated into chewable tablets and liquid aqueous suspensions for medicinal use. Both cellulose acetate phthalate and gelatin are the micro-encapsulating polymer wall materials.

Control of pH, controlled addition of a Hofmeister (lyotropic) salt, microencapsulation of the water-insoluble NSAID medicament with a liquid phase of both cellulose acetate phthalate and gelatin microencapsulating material, and the subsequent insolubilization of said liquid encapsulating material after it is wrapped around the medicament core with dilute acid and crosslinking agent are important process parameters to achieving the proper individual microcapsules to obtain highly bioavailable, taste-masked, water-insoluble NSAID drug materials, e.g., naproxen and ibuprofen, by microencapsulation alone.

BACKGROUND OF THE INVENTION AND PRIOR ART

Non-steroidal anti-inflammatory drugs (NSAID) having analgesic and anti-inflammatory properties have been widely administered orally in the treatment of mild to severe pain, particularly for rheumatoid arthritis and osteoarthritis patients. Tolerance or addiction to these drugs is not generally a problem with their continuous use in the treatment of pain or in the treatment of acute or chronic inflammatory states. However, these drugs generally have a higher potential for adverse side effects at the upper concentrations (limits) of their effective dose ranges. Therefore, it is important that such non-steroidal anti-inflammatory drugs be accurately measured and administered orally.

These non-steroidal anti-inflammatory drugs, e.g., ibuprofen and naproxen, have been widely prescribed by physicians. These drugs are in general tolerated well by most patients and provide an effective means for control of pain and inflammatory processes, particularly for the rheumatoid arthritis and osteoarthritis patients. However, these non-steroidal anti-inflammatory drugs impart a burning sensation, have a bitter taste and aftertaste, and/or have an adverse mouth feel when taken orally.

Therefore, in order to make wider use of them while substantially eliminating the bitter taste, aftertaste and adverse mouth feel and make these drugs more pleasant upon taking them orally, there has long been desired a way to insure delivery of these drugs in their desired concentrations while avoiding their extremely bitter taste, lingering aftertaste and adverse mouth feel effects referred to above connected with their ingestion orally, thereby encouraging patient compliance.

Various ways and delivery systems have been attempted in the prior art to accomplish these and other objectives.

One such system is described in co-pending application of Thomas C. Powell and Massimo M. Calanchi Ser. No. 819,609, filed Jan. 9, 1992 and entitled "Microencapsulated Taste-Masked Water Insoluble NSAID Drug Materials". That application is directed to preparation of individual taste-masked, high payload, microcapsules by microencapsulation of water-insoluble NSAID drug materials in the substantial absence of microcapsule agglomerates. These taste-masked microcapsules contain a high payload, e.g., about 83+ wt. % of said NSAID drug material and can be formulated into chewable tablets and liquid aqueous suspensions for medicinal use. Cellulose acetate phthalate is the sole micro-encapsulating polymer wall material.

Another such system is described by J. R. Nixon et al in an article entitled "The In Vitro Evaluation of Gelatin Coacervate Microcapsules" appearing in J. Pharm. Pharmac, 1971, 23 Suppl. 147S-155S. This article describes the microencapsulation of sulfadiazine with gelatin using sodium sulphate as the coacervation agent. The free flowing microcapsular material was hardened with formalin, although other hardening agents such as glutaraldehyde and acrolein could be used as cross linking agents. In vitro dissolution studies were carried out.

U.S. Pat. No. 4,766,012, issued to Valenti, teaches the microencapsulation of ibuprofen and naproxen. The microencapsulation method employed by Valenti involves dissolving a coating agent in water by salification to form an aqueous solution, dispersing the medicament particles first in water, then in the solution of salified coating agent to form a suspension, and adding an acidifying agent to precipitate the coating agent onto the particles of medicament and recovering the microcapsules thus formed.

U.S. Pat. No. 4,460,563, issued to Massimo Calanchi, discloses the microencapsulation of ibuprofen with hydroxypropylmethylcellulose phthalate.

U.S. Pat. Nos. 4,835,186; 4,835,187; and 4,835,188 are directed to making taste-neutral (taste-masked) ibuprofen in dry powder form. U.S. Pat. Nos. 4,835,186 and 4,835,187 involve obtaining this taste-neutral ibuprofen in powder form by spray drying suspensions of colloidal silica in organic solvent solutions of ibuprofen and a cellulose material.

In U.S. Pat. No. 4,835,186, issued to Gerald L. Reuter et al, the organic solvent is a mixture of lower alkanol, e.g., isopropanol, and ethyl acetate, and the cellulose material is cellulose acetate phthalate. This product is stated to contain about 40% to 70% by weight ibuprofen, about 15% to 50% by weight of cellulose acetate phthalate and about 5% to 40% by weight colloidal silica.

In U.S. Pat. No. 4,835,187, issued to Gerald L. Reuter et al, the organic solvent is a lower alkanol, e.g., isopropanol, or contains at least 50% lower alkanol, and the cellulose material is ethyl cellulose, hydroxyethyl cellulose, or hydroxypropylmethyl cellulose, alone or in admixture. The lower alkanol solvent has a colloidal silica suspended therein. This product is stated to contain about 40% to 70% by weight ibuprofen, about 15% to 50% of a cellulose material selected from the group consisting of ethyl cellulose, hydroxyethyl cellulose, hydroxypropylmethyl cellulose and admixtures thereof and about 5% to 40% by weight colloidal silica.

In U.S. Pat. No. 4,835,188, issued to Ying T.R. Ho et al, the taste-neutral powder form of ibuprofen is obtained by spray drying a dispersion of ibuprofen and ethyl cellulose in water having a plasticizer dissolved or suspended therein. This powder is stated to contain about 63% to 77% by weight ibuprofen, about 25% to 40% by weight ethyl cellulose and about 2% to 7% weight plasticizer.

An article by H. P. Merkle et al entitled "Preparation and In Vitro Evaluation of Cellulose Acetate Phthalate Coacervate Microcapsules", J. Pharm Science 62 pp. 1444–1448 (1973) describes the microencapsulation of phenacetin by coacervation of aqueous cellulose acetate phthalate using sodium sulfate as the coacervating agent. The article in column 1 on page 1444 refers to other literature describing coacervate encapsulation, a common preparation technique being either simple coacervation of gelatin with ethanol or sodium sulfate as dehydrating agents or complex coacervation of gelatin acacia mixtures. The statement is made by the authors that "Coacervation methods with pure gelatin and mixtures are rather complicated and difficult to control, particularly with regard to the hardening of the shells and the recovery of the microcapsules". In the last complete paragraph in column 1 on page 1448, the authors refer to other literature as showing an extremely rapid initial release from gelatin coacervate microcapsules.

The present invention provides a method of simultaneously encapsulating ibuprofen using both gelatin and cellulose acetate phthalate as the encapsulating material to give the microcapsules a dual coating, the gelatin portion of the coating providing high bioavailability of the ibuprofen core and the cellulose acetate phthalate providing the taste-masking effect. The gelatin in the dual coating serves to temper the well known delayed release properties of the cellulose acetate phthalate without interfering with its taste-masking function.

DETAILED DESCRIPTION OF THE INVENTION

This invention enables the preparation of individual taste-masked high bioavailability microcapsules by microencapsulation of water-insoluble NSAID drug materials in the substantial absence of microcapsule agglomerates, viz., agglomerates of individual microcapsules. These taste-masked highly bioavailable individual microcapsules can then be formulated into chewable tablets and liquid aqueous suspensions of the appropriate dosage for medicinal use. Both cellulose acetate phthalate and gelatin are the microencapsulating polymer microcapsule wall materials.

Control of pH, controlled addition of a Hofmeister (lyotropic) salt, simultaneous microencapsulation of the water-insoluble NSAID medicament with a liquid phase of both cellulose acetate phthalate and gelatin polymer material and the subsequent insolubilization of said liquid microencapsulating material, after it has wrapped around the medicament core, with glutaraldehyde and dilute acid are important process parameters to achieving the proper individual microcapsules to obtain these highly bioavailable, taste-masked water-insoluble NSAID drug materials by microencapsulation alone. These individual microcapsules thus obtained are bland tasting, however, and use of flavoring agents to impart pleasant tastes to the already effectively taste-masked water-insoluble NSAID drug materials is preferred when formulating same into chewable tablets and liquid suspension oral dosage forms.

Usually the average/mean microcapsule diameter ranges from about 25 to about 600 microns. The process of this invention involves the principal steps of preparing an aqueous dispersion of the water-insoluble non-steroidal, anti-inflammatory drug (NSAID) material within an aqueous solution of cellulose acetate phthalate, said water-insoluble NSAID drug material particles having a particle size ranging from about 25 to about 500 microns at a pH of about 6 or higher wherein said solution contains from about 2 to about 8 wt. % of cellulose acetate phthalate; heating the aqueous dispersion with agitation to a temperature sufficient to dissolve gelatin; adding a solution of gelatin; gradually adding with continued agitation a solution containing an inorganic Hofmeister (lyotropic) salt to form both cellulose acetate phthalate and gelatin in liquid phase separate from the equilibrium liquid; slowly lowering the temperature of the dispersion to about 30° C. then dropping the temperature rapidly to about 15° C.; gradually adding a solution of glutaraldehyde; and after about 60 minutes slowly adjusting the pH of the resulting solution by slow addition of a dilute acid to a pH of about 4 or lower which renders said cellulose acetate phthalate polymer insoluble; and recovering the individual microcapsules thus formed.

The term inorganic Hofmeister (lyotropic) salt as used herein refers to the sulfate, citrate, tartrate, acetate, chloride, nitrate, bromide and iodide anion salts of sodium, potassium, ammonium, rubidium, cesium, magnesium, calcium, silicone, barium and lithium cations. Sodium sulfate is preferred.

Various aldehydes can be used as cross-linking agents instead of glutaraldehyde and these include, for example, formalin and acrolein.

While various dilute acids can be used to insolubilize the cellulose acetate phthalate polymer cell wall material, e.g., citric acid, acetic acid, fumaric acid, tartaric acid, etc., the use of citric acid is preferred for this purpose in a concentration of about 10 to about 30 wt. % in water.

Suitable water-insoluble NSAID drug materials which can be used in accordance with this invention include, but are not necessarily limited to, the following: naproxen, ibuprofen, sulindac, diclofenac, fenclofenac, alclofenac, ibuprofen, isoxepac, furofenac, tiopinac, zidometacin, acemetacin, fentiazac, clidanac, oxipinac, zomepirac sodium and pharmaceutically acceptable water-insoluble salts thereof.

The taste-masked individual microcapsules of water-insoluble NSAID drug material produced in accordance with this invention contain a high payload of the water-insoluble NSAID drug core material, e.g., about 83+ wt. %, based on total microcapsule weight.

The gelatin used in the invention can be of any origin so long as it is of pharmaceutical grade. The gelatin, for example, can have a number average molecular weight of about 27,000 to 70,000 with a Bloom number of about 55 to 325, an isoelectric point of about 5.0 to 9.2, and a viscosity of about 6 to 8 cps at 40° C. The gelatin can be acid pretreated material which has been deionized or alkali processed Hide gelatin, also deionized. Preferably the gelatin is of USP or NF grade.

The relative amounts of gelatin and cellulose acetate phthalate used can vary depending on the bioavailability and the degree of taste-masking desired for the particular NSAID being encapsulated.

This invention will be illustrated in greater detail in the examples which follow.

EXAMPLE 1

(Preparation of Cellulose Acetate Phthalate (CAP) and Gelatin Microencapsulated Ibuprofen)

In a 2-liter beaker there are added 656 grams of deionized water. With agitation, 9 grams of sodium bicarbonate were added to adjust the pH so as to solubilize the cellulose acetate phthalate polymer. To this solution 35 grams of particulate cellulose acetate phthalate having a particle size of about 14 mesh to 200 mesh, and more particularly about 1200 microns to about 50 microns, were added in small increments with continued agitation over 8–12 hours until all of the cellulose acetate phthalate (CAP) is added and dissolved. The resulting solution contains 5 weight percent cellulose acetate phthalate and has a pH of about 7.0 or slightly above.

To a 1500 ml beaker there were added 300 grams of the above CAP solution, 300 grams of deionized water, and 3 grams of a 5% aqueous solution of sodium lauryl sulfate: Ibuprofen in the amount of 150 grams (sieved—30 mesh) was added slowly with stirring resulting in a pH of about 6 at 30° C. The admixture was heated to 40° with continued stirring and then defoamed. To the admixture was then added 150 grams of a 10% aqueous Type A gelatin solution and the pH was about 6.2 at 37° C.

With continued agitation, there were added slowly dropwise from a separatory flask (250 ml) of a 20% by weight aqueous solution of sodium sulfate over a period of 40-50 minutes. This sodium sulfate solution acts as a coacervating agent permitting the gelatin and the cellulose acetate phthalate polymer to come out as a liquid phase microencapsulating material wrapping the drug particles. The dispersion temperature is then allowed to drop slowly from 40° C. to 30° C. in 30–60 minutes and then the temperature is dropped quickly to 10° C. The pH of the mixture is then adjusted to 6.0 with 10% aqueous citric acid. At this time 75 grams of a 25% glutaraldehyde solution is added to cross-link the gelatin in the microcapsules and thus enable drying. The temperature is raised to 20° C. in one hour after the glutaraldehyde addition and the pH of the dispersion is lowered to 3.5 by addition of a 10% aqueous citric acid solution thereby rendering the cellulose acetate phthalate and the gelatin insoluble at that pH. The microcapsule dispersion is heated to 25° C. in one hour and stirred overnight (16–24 hours). The microcapsules are then allowed to settle and the manufacturing medium is decanted. Fresh wash water in the amount of 1500 milliliters is then added and the microcapsule dispersion is stirred for five minutes. The washing process is repeated three times and the microcapsules are then vacuum filtered and dried in a tray dryer. The microcapsules are sieved through a 20 mesh (840 μ) screen and 9.2 grams were oversize. The yield was 177.1 grams, or 97.4%. The microcapsules had an ibuprofen payload of 83 + weight percent.

EXAMPLE 2

(Formulation of Chewable Tablets Containing the CAP and Gelatin Microencapsulated Ibuprofen Prepared According to Example 1)

The following materials are added in the following proportions to a laboratory V-blender and blended for twenty minutes. The proportions are for a 50 milligram (active) tablet.

|  | mg/tab |
|---|---|
| Ibuprofen Gelatin/CAP microcaps | * |
| Mannitol Granules, USP | ** |
| Aspartame, NF | 10.0 |
| Grape Flavor, Artificial | 3.0 |

-continued

|  | mg/tab |
|---|---|
| Citric Acid, Fine Granular USP | 1.5 |
| Crospovidone, NF | 0.8 |
| D&C Red #27 | 0.8 |
| FD&C Blue #1 | 0.1 |
| Talc | 8.0 |
| Colloidal Silicon Dioxide | 6.0 |
| Magnesium Stearate | 2.5 |
|  | 325. |

The tablet weight is fixed by allowing for variation in the amounts of microcapsules and Mannitol Granules, USP used.

After blending the above materials for 20 minutes, a small portion of the blend is removed into a container and magnesium stearate is added thereto. The materials are mixed by hand and returned to the V-blender and blended for 5–10 minutes.

Tablets are compressed from this mixture on a Stokes RB2 rotary press with ⅜ inch round, beveled edge, scored tooling. These tablets had satisfactory hardness and friability.

The amount of ibuprofen gelatin/CAP microcapsules needed depends on the active content or assay of the microcapsules. This amount can be calculated with the following equation.

$$\text{amount of microcapsules (mg/tab)} = \frac{\text{desired active content (mg/tab)}}{\text{assay (\%)/(100)}}$$

The amount of Mannitol Granules, USP needed is equal 291.675 mg/tab—amount of microcapsules needed. Since this formula is dose proportional, the desired active content can be obtained by multiplying all ingredient amounts by the appropriate factor. The active content or assay of the ibuprofen microcapsules of Example 1 is 83% by weight of microcapsule. Hence for 50 milligram active chewable tablets, the amount of microcapsules in the above formulation is $$\frac{50}{83\%/100}$$

=60.24 milligrams of ibuprofen gelatin/CAP microcaps and the amount of mannitol granules required is 291.675−60.24=231.435 milligrams

EXAMPLE 3

(Preparation of Cellulose Acetate Phthalate (CAP) and Gelatin Microencapsulated Ibuprofen)

Into a 3-liter beaker fitted with a birdcage baffle and a stirring motor with a 3" turbine blade, were added 90 grams of CAP into 1687 ml. of deionized water. The batch was stirred overnight.

With agitation, 23 grams of sodium bicarbonate was added to adjust the pH so as to solubilize the CAP. The CAP has a particle size of about 40 mesh to 200 mesh. Three grams of sodium lauryl sulfate dissolved in 57 grams of water were added with stirring and the CAP particles were well dispersed to facilitate dissolving the CAP polymer. The resulting solution contains 5 wt. % CAP and has a pH of about 7.0 or slightly above.

Next, 500 g of ibuprofen were dispersed into the CAP solution. The ibuprofen particles had a particle size of approximately 25 to 500 microns. As a defoamer, 5 grams of simethicone emulsion in 45 grams of water was added and then 210 grams of gelatin Type A dissolved in 1890 grams of water (10% solution) were added with stirring.

The sodium sulfate solution comprising 860 grams of sodium sulfate dissolved in 2440 grams of water (26% solution) was added slowly (dropwise) with continuous agitation at about 150 rpm. This addition takes place over approximately 1–½ hours. This sodium sulfate aqueous solution acts as a coacervating agent permitting the CAP polymer and the gelatin to come out as liquid phase microencapsulating materials wrapping the ibuprofen drug particles. During the sodium sulfate addition the mixture was slowly cooled from 40° C. to 30° C. and then fast cooled to 10° C.

After the CAP gelatin liquid microcapsule walls are formed, the CAP polymer was rendered insoluble by slow addition of 500 grams of an 10% aqueous citric acid solution until the final solution pH is approximately 4, thus rendering the CAP insoluble at that pH for water. At this point a 50% aqueous solution of glutaraldehyde in the amount of 52.5 milliliters was added to cross-link the gelatin and the mixture was heated to 20° C. and then stirred overnight. Once this has been accomplished, the agitation is stopped and the microcapsules are allowed to settle from solution so that the supernatant liquid may be decanted.

These individual microcapsules of ibuprofen were then washed with 6 kilograms of water and washed four times more with 8 kilogram portions of water. The washed CAP and gelatin walled microencapsulated ibuprofen microcapsules were then filtered by a vacuum filter and dried using a fluid bed dryer at a temperature of 30° C. for a period of about 1–2 hours. These individual beige free flowing microcapsules contain approximately 83 wt. % ibuprofen.

EXAMPLE 4

(Microencapsulation of Naproxen with Cellulose Acetate Phthalate (CAP) and Gelatin)

Naproxen is microencapsulated with cellulose acetate phthalate and gelatin using the same procedure and concentrations as set forth in Example 1 except that naproxen is used in place of ibuprofen. The naproxen individual microcapsule core payload is approximately 83 wt. % with the remainder being cellulose acetate phthalate and gelatin microcapsule wall material.

EXAMPLE 5

(Preparation of a Liquid Suspension Containing the Cap and Gelatin microencapsulated Ibuprofen Prepared According to Example 1)

The CAP and gelatin microencapsulated ibuprofen microcapsules prepared in accordance with Example 1 above were then formulated into a liquid suspension dosage form. The preparation of the liquid suspension dosage form was accomplished as follows:

Four (4) liters of liquid suspension vehicle were prepared by the following procedures:

All of the following ingredients were dry blended:
800 grams of sucrose,
20 grams of sodium carboxymethylcellulose,
4.8 grams of xanthan gum,
4.8 grams of sodium saccharin,
46.5 milligrams of FD&C Yellow #5, and
103.5 milligrams of FD&C Yellow #6

The above dry blended materials were then dissolved in approximately 1500 ml of purified water in a 4-liter beaker with agitation. Then 4.8 grams of methyl paraben and 1.2 grams of propyl paraben were dissolved in 40 ml of USP propylene glycol and added to the above water solution. Then the following materials were added sequentially in their noted amounts:

1200 grams of light corn syrup,
8 ml of orange flavor oil,
2 grams of Tween 80, and
40 ml of a 20% (W/V) aqueous solution of citric acid.

All ingredients were allowed sufficient time to mix and then there was added a sufficient quantity of purified water to bring the volume to 4 liters.

2.4 grams of the high payload (83%) CAP and gelatin microencapsulated individual ibuprofen microcapsules prepared in accordance with Example 1 were added to 100 ml of the liquid suspension vehicle produced as indicated above to form a liquid suspension dosage form of microencapsulated ibuprofen.

We claim:

1. A process for preparing microencapsulated nonsteroidal, anti-inflammatory, water-insoluble NSAID drug material which comprises:

(a) preparing an aqueous dispersion of said NSAID material having a particle size distribution ranging from about 25 to about 500 microns within an aqueous solution of cellulose acetate phthalate at a pH of about 6 or higher and containing from about 2 weight percent to about 8 weight percent of cellulose acetate phthalate;

(b) heating with agitation the aqueous dispersion of said NSAID material in the aqueous solution of cellulose acetate phthalate to a temperature sufficient to dissolve gelatin;

(c) adding an aqueous solution of gelatin to the heated dispersion of said NSAID material in the aqueous solution of cellulose acetate phthalate;

(d) gradually adding with continued agitation a solution containing an inorganic salt of the Hofmeister (lyotropic) series, to form both cellulose acetate phthalate and gelatin in liquid phase separate from the equilibrium liquid;

(e) slowly lowering the temperature of the dispersion to about 30° C. then dropping the temperature rapidly to about 15° C.;

(f) gradually adding a solution of glutaraldehyde to the cooled dispersion and after about 60 minutes;

(g) slowly adjusting the pH of the resulting solution to a pH of about 4 or lower while rendering said cellulose acetate phthalate polymer and the gelatin insoluble by slow addition of a dilute acid material and recovering the individual microcapsules thus formed.

2. A process as in claim 1 wherein said water-insoluble NSAID drug material is naproxen.

3. A process as in claim 1 wherein said water-insoluble NSAID drug material is ibuprofen.

4. A process as in claim 1 wherein said Hofmeister (lyotropic) salt is sodium sulfate.

5. A process as in claim 1 wherein said dilute acid material is citric acid.

* * * * *